US012508429B2

(12) United States Patent
Doerr et al.

(10) Patent No.: US 12,508,429 B2
(45) Date of Patent: Dec. 30, 2025

(54) MEDICAL SYSTEM FOR PERFORMING A THERAPEUTIC FUNCTION ON A PATIENT

(71) Applicant: BIOTRONIK SE & Co. KG, Berlin (DE)

(72) Inventors: Thomas Doerr, Berlin (DE); Sergey Ershov, Berlin (DE); Torsten Radtke, Berlin (DE); Uwe Kamenz, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 676 days.

(21) Appl. No.: 17/922,612

(22) PCT Filed: Apr. 28, 2021

(86) PCT No.: PCT/EP2021/061118
§ 371 (c)(1),
(2) Date: Nov. 1, 2022

(87) PCT Pub. No.: WO2021/224087
PCT Pub. Date: Nov. 11, 2021

(65) Prior Publication Data

US 2023/0166114 A1 Jun. 1, 2023

(30) Foreign Application Priority Data

May 6, 2020 (EP) .................................... 20173116

(51) Int. Cl.
*A61N 1/37* (2006.01)
*A61N 1/372* (2006.01)

(52) U.S. Cl.
CPC ........... *A61N 1/37* (2013.01); *A61N 1/37247* (2013.01)

(58) Field of Classification Search
CPC .... A61N 1/37; A61N 1/37247; A61N 1/3925; A61N 1/3718
See application file for complete search history.

(56) References Cited

U.S. PATENT DOCUMENTS 9,364,663 B2 6/2016 Doerr et al.
9,981,124 B2 5/2018 Jenison et al.
(Continued)

FOREIGN PATENT DOCUMENTS

WO 2010062978 A2 6/2010

OTHER PUBLICATIONS

International Search Report (PCT/ISA/210) and Written Opinion (PCT/ISA/237) mailed on Jul. 23, 2021, by the European Patent Office as the International Searching Authority for International Application No. PCT/EP2021/061118.

*Primary Examiner* — Eugene T Wu
(74) *Attorney, Agent, or Firm* — Buchanan Ingersol & Rooney PC

(57) ABSTRACT

A medical system for performing a therapeutic function on a patient comprises an implantable medical device having a switching function to switch from a normal operating mode to an MRI compatible operating mode in the presence of an MRI device, and an external device for programming at least one setting of the implantable medical device. The external device is configured, based on a programming event relating to said at least one setting, to generate a notification prompting a user to confirm a continuing MRI compatibility of said MRI compatible operating mode after the programming event and/or to amend said at least one setting for achieving MRI compatibility.

13 Claims, 4 Drawing Sheets

(56) References Cited

U.S. PATENT DOCUMENTS

| | | | | |
|---|---|---|---|---|
| 2006/0167496 | A1 * | 7/2006 | Nelson | A61N 1/37235 607/2 |
| 2007/0255332 | A1 | 11/2007 | Cabelka et al. | |
| 2010/0137947 | A1 * | 6/2010 | Gadagkar | G16H 40/40 607/60 |
| 2011/0077706 | A1 | 3/2011 | Ellingson et al. | |
| 2011/0137359 | A1 | 6/2011 | Stubbs et al. | |
| 2013/0053920 | A1 | 2/2013 | Lalonde et al. | |

* cited by examiner

MEDICAL SYSTEM FOR PERFORMING A THERAPEUTIC FUNCTION ON A PATIENT

CROSS-REFERENCE TO RELATED APPLICATIONS

This application is the United States National Phase under 35 U.S.C. § 371 of PCT International Patent Application No. PCT/EP2021/061118, filed on Apr. 28, 2021, which claims the benefit of European Patent Application No. 20173116.3, filed on May 6, 2020, the disclosures of which are hereby incorporated by reference herein in their entireties.

TECHNICAL FIELD

The present invention relates to a medical system according to the preamble of claim 1, to an external device and to a method for operating a medical system.

BACKGROUND

A medical system of this kind may, for example, serve for providing a therapeutic function on a patient, such as a stimulation function, for example, a cardiac pacing function or a neurostimulation function.

An implantable medical device in this context may, for example, be a pacemaker device for providing for a pacing action in a patient's heart, e.g., a CRT device, or a defibrillator device, such as an implantable cardioverter-defibrillator (ICD), for providing for a defibrillation, a neuro-stimulation device or generally an implantable pulse generator for generating stimulation pulses.

An implantable medical device, for example, a stimulation device such as a pacemaker device or a defibrillator device, generally is configured to output electrical stimulation energy for performing a therapeutic stimulation action. An implantable medical device in addition may be configured to sense electrical signals relating, e.g., to cardiac activity, in particular to trigger and clock a stimulation action. If an implantable medical device is introduced into an electromagnetic field of an MRI device, it can be assumed that electrical signals are induced on leads and other conducting parts of the implantable medical device, such electrical signals causing a disturbance of the operation of the medical device. For example, for an implantable medical device in the shape of a pacemaker device or a defibrillator device, a disturbance of a stimulation action may cause an erroneous stimulation and hence may have a significant impact on a therapy of a patient, which needs to be avoided.

There hence is a general need to detect whether a patient carrying an implantable medical device is in the vicinity of an MRI device, such that, if this is the case, operation of the medical device may be modified in order to reduce a risk for a malfunction of the implantable medical device.

U.S. Pat. No. 9,364,663 B2 discloses an implantable medical device including a power supply, a sensing device and/or a stimulation device. An MR detection unit may identify an MR-typical journey of an implantable medical device on a patient bed of an MRI device, based on a change over time of measurement values of at least two magnetic field sensors and a difference between the measured values of the at least two magnetic field sensors. Herein, if measurement values of the at least two magnetic field sensors exceed a threshold, a presence of an MRI device is assumed.

U.S. Pat. No. 9,981,124 B2 discloses an implantable medical device having a first magnetic field direction sensor located at a first location within a housing and configured to generate a signal representative of a first direction of a magnetic field at the first location, and a second magnetic field direction sensor located at a second location within the housing and configured to generate a signal representative of a second direction of the magnetic field at the second location. Based on signals obtained via the first magnetic field direction sensor and the second magnetic field direction sensor it is concluded for a presence of an MRI device.

U.S. Publication No. 2011/0077706 A1 discloses an implantable medical device which automatically determines at least a portion of the parameters of an exposure operating mode based on stored information regarding sensed physiological events or therapy provided over a predetermined period of time. The implantable medical device may configure itself to operate in accordance with the automatically determined parameters of the exposure operating mode in response to detecting a destructive energy field. Alternatively, the implantable medical device may provide the automatically determined parameters of the exposure operating mode to a physician as suggested or recommended parameters for the exposure operating mode.

In case a patient carrying an implantable medical device such as a pacemaker device or a defibrillator device shall undergo an MRI examination, nowadays it is conventional practice that a patient prior to undergoing the MRI examination has to visit a physician such that the physician may adapt operation of the implantable medical device using an external programming device. For example, the physician may enable, using the external programming device, an MRI compatible operating mode in which a stimulation function of the implantable medical device is switched off or is modified in order to reduce a risk of malfunction in the presence of an electromagnetic field caused by an MRI device, for example, the MRI device's constant magnetic field, the device's gradient field or the device's RF field. The physician herein may enable the respective MRI compatible mode, such that the MRI compatible mode may be switched on once the implantable medical device is brought into proximity with an MRI device, wherein the actual activation of the MRI compatible mode may take place automatically by a suitable detection within the implantable medical device.

Using an external device, also other settings of the implantable medical device may be changed, wherein settings generally relate not only to the normal operating mode, but may also affect the MRI compatible operating mode. For example, following an invasive change of the hardware configuration of an implantable medical device, for example, when adding an electrode to an implantable medical device such as a pacemaker device or when removing or replacing an electrode of the implantable medical device, a change in the settings of the implantable medical device is generally required in order to adapt operation of the implantable medical device to the new hardware configuration. The change in the settings may affect both the normal operating mode and the MRI compatible operating mode, as also the new hardware configuration may affect both the normal operating mode and the MRI compatible operating mode.

International Publication No. 2010/062978 A2 discloses a system including a processor configured to automatically obtain magnetic resonance imaging compatibility information relating to compatibility of an active implantable medical device with an MRI modality from at least two information sources. Based on the information, compatibility may automatically be determined.

The present disclosure is directed toward overcoming one or more of the above-mentioned problems, though not necessarily limited to embodiments that do.

SUMMARY

It is an object of the instant invention to provide a medical system, an external device and a method for operating a medical system which may facilitate to achieve MRI compatibility even after a change in settings of an implantable medical device.

At least this object is achieved by means of a system comprising the features of claim 1.

Accordingly, the system comprises an implantable medical device having a switching function to switch from a normal operating mode to an MRI compatible operating mode in the presence of an MRI device, and an external device for programming at least one setting of the implantable medical device. The external device is configured, based on a programming event relating to said at least one setting, to generate a notification prompting a user to confirm a continuing MRI compatibility of said MRI compatible operating mode after the programming event and/or to amend said at least one setting for achieving MRI compatibility.

Using the external device, a user may access the implantable medical device for changing one or multiple settings of the implantable medical device. A change in setting herein takes place in a programming event, in which a user, for example, uses a programming interface of the external device to program a respective setting, wherein after the programming the change of settings is effected within the implantable medical device, and the implantable medical device from thereon operates according to the changed settings.

As a change in settings may affect both a normal operating mode and an MRI compatible operating mode, the external device is configured to generate a notification which prompts a user to confirm a continuing MRI compatibility of the MRI compatible operating mode after the programming event or to amend the setting for achieving MRI compatibility. Following a programming event in which one or multiple settings are changed, a user hence is prompted to confirm a continuing MRI compatibility of the MRI compatible operating mode, or—in particular if the user cannot confirm the continuing MRI compatibility—to amend the settings to achieve MRI compatibility of the MRI compatible operating mode.

As a change in settings in particular may also affect MRI compatibility, the user by the notification is forced to evaluate MRI compatibility, such that a confirmation of a continuing MRI compatibility is obtained from the user, and the implantable medical device hence may be operated in an MRI compatible fashion even after the change in settings.

A confirmation for a continuing MRI compatibility in the instant text is to be understood as a confirmation by a user that the MRI compatible operating mode is still MRI compatible even after the change in settings as it has taken place during the programming event. The MRI compatible operating mode generally is programmed to be MRI compatible, such that operation of the implantable medical device in the presence of an MRI device takes place in a way that operation of the implantable medical device is not disturbed or otherwise affected by the presence of the MRI device. As the change in settings may affect the MRI compatibility of the device, the user is asked to confirm that even after the change in settings the MRI compatible operating mode continues to be MRI compatible.

Hence, if in the presence of an MRI device the implantable medical device is switched to the MRI compatible operating mode, the implantable medical device may operate in a way such that it is compatible with the MRI device and does not exhibit any malfunctions, in particular any erroneous simulations due to an interaction with electromagnetic fields of the MRI device.

In one embodiment, the external device comprises a display device for visually outputting the notification. Whereas the implantable medical device, in an implanted state, is placed within a patient, the external device remains outside of the patient and may communicate with the implantable medical device in a wireless fashion, for example, using telemetry. The external device comprises a display device, which allows for a visual output of the notification prompting the user to confirm an MRI compatibility of an MRI compatible operating mode, or otherwise to change respective settings in order to establish MRI compatibility of the MRI compatible operating mode.

The notification may be a text message displayed, for example, on the display device. The notification in addition or alternatively may come with a visual alarm signal, such as a blinking color field or the like.

Alternatively or in addition, the external device may comprise another output device, such as an acoustic output or a printing device, or may communicate with further devices for outputting the notification.

The external device in addition may comprise an input device such as a keyboard or the like to allow an input of information, in particular for inputting a confirmation in reaction to the notification or for changing one or multiple settings to establish MRI compatibility.

In one embodiment, the programming event may relate to a change in a hardware configuration of the implantable medical device. Such hardware configuration may take place while the implantable medical device is implanted in a patient, for example, in that an electrode is added to or removed from the implantable medical device. In this case also an adaption of the settings of the implantable medical device may be required in order to adapt operation of the implantable medical device, taking into account, e.g., the new electrode configuration. The change of settings takes place in one or multiple programming events using the external device, wherein the programming typically is done by a physician which accesses the implantable medical device via the external device for effecting the change in settings.

In one embodiment, the programming event relates to a change in a software configuration of the implantable medical device. The change in software configuration may, for example, relate to a modification of a therapeutic or diagnostic function, for example, a stimulation function such as a pacing function, a defibrillator function or an atrial anti-tachycardia pacing (ATP) function. In addition or alternatively, a change in software configuration may relate to a change from a synchronous stimulation mode to an asynchronous stimulation mode or vice versa, which is effected by a change in settings as programmed on the external device. Furthermore, the programming event relates, for example, to functions like the power management of the medical device, or the electrode vector for delivery of therapeutic or diagnostic energy, or the sensitivity setting of the sensing function, or the remote monitoring function, or the telemetry settings of the medical device, or patient related data stored in the device (like a risk score).

In one embodiment, the external device is configured to affect said at least one setting of the implantable medical device only if the continuing MRI compatibility of said MRI compatible operating mode is confirmed by a user in reaction to the notification. If a user changes a particular setting of the implantable medical device on the external device, the external device generates the notification asking the user to confirm the continuing MRI compatibility of the MRI compatible operating mode. Only if this confirmation is entered by the user, the setting as set and programmed by the user is activated such that the implantable medical device may operate according to the changed setting. If, however, the user does not enter a confirmation, the setting is not activated, such that the implantable medical device may continue to operate according to prior settings.

The notification herein may be displayed or otherwise output in an enduring fashion to the user as long as no confirmation is entered. For example, the notification may be continuously displayed on a display device of the external device as long as the continuing MRI compatibility of the MRI compatible operating mode is not confirmed by the user, such that the user is forced to enter the confirmation or otherwise change the settings such that the MRI compatibility may be confirmed.

In one embodiment, the implantable medical device comprises a sensing device for sensing a measurement quantity indicative of a presence of an MRI device, and a processing device for controlling operation of the implantable medical device and for identifying a presence of an MRI device based on measurement values obtained from the sensing device.

In one embodiment, the implantable medical device comprises a program memory configured to store at least one program routine for operating the implantable medical device in case of a presence of an MRI device, wherein the processing device is configured, for controlling operation of the implantable medical device in the presence of an MRI device, to switch from the normal operating mode to said at least one program routine, the at least one program routine implementing the MRI compatible operating mode.

Operation of the implantable medical device is controlled by the processing device, which, for controlling the operation, uses a software program defining the mode of operation of the implantable medical device. Herein, in general operation of the implantable medical device a normal operating mode is employed for providing, e.g., a stimulation function, such as a pacemaker function of a pacemaker device, a defibrillator function of a defibrillator device or a neuro-stimulation function of a neuro-stimulation device.

In general, the normal operating mode may be based, e.g., on a triggered, synchronous stimulation, involving a detection of activity, e.g., cardiac activity, such that a pacemaker function, for example, is triggered in a synchronous manner with cardiac activity. The normal operating mode may, for example, be a so-called VVI mode, relating, for example, to a ventricular anti-bradycardia pacing, or a DDD mode, relating, for example, to a dual-chamber anti-bradycardia pacing.

If, by means of measurements obtained from the sensing device, the processing device identifies the presence of an MRI device, for example, due to a rise of the magnetic fields as measured by the sensing device, the processing device is configured to switch to a program routine which is specifically adapted for operation of the implantable medical device in the presence of an MRI device. Herein, in a program memory of the implantable medical device multiple, for example, different program routines may be stored, each program routine defining a specific operation of the implantable medical device suitable for operating the implantable medical device in the presence of an MRI device and hence representing an MRI compatible operating mode.

Generally, within the presence of an MRI device, a stimulation function should be adapted such that the electromagnetic fields of the MRI device do not give rise to a malfunction of the implantable medical device. Hence, the program routine is adapted such that a stimulation function is modified and no erroneous stimulation is triggered by a potential signal induction caused by an electromagnetic field of the MRI device.

It is to be noted that the at least one program routine may be implemented by software and may, for example, be part of the general operating software of the processing device for controlling operation of the implantable medical device. Program routines hence may be implemented as different, e.g., modular software functions which are part of the software of the processing device.

The switching to an MRI compatible program routine takes place once the processing device identifies the presence of an MRI device, based on measurements obtained from the sensing device, for example, based on measurements of a magnetic field strength. Hence, as soon as an MRI device is present, the processing device switches to a program routine which specifically is adapted for operation in the presence of an MRI device, such that a malfunction of the implantable medical device during an MRI examination is avoided. As soon as it is identified, again based on measurements from the sensing device, that the MRI device no longer is present, the processing device may switch back to the normal operating mode, hence resuming the normal operation of the implantable medical device.

In one embodiment, the MRI compatible program routine represents an OFF mode in which a stimulation function is switched off. Hence, in the presence of an MRI device the processing device may select a program routine in which a stimulation function is switched off, such that no stimulation takes place in case a patient undergoes an MRI examination.

In one embodiment, the MRI compatible program routine may represent an asynchronous mode employing an asynchronous stimulation. Within such asynchronous stimulation, a stimulation without a triggering based on a sensing of, e.g., cardiac activity takes place, such that an erroneous triggering is avoided due to interaction with the MRI device's electromagnetic fields.

The program routine representing the asynchronous mode may, for example, employ a so-called DOO or VOO mode, wherein also different program routines for carrying out a DOO mode and a VOO mode may be present. In a DOO mode an asynchronous atrial and ventricular pacing may take place. In a VOO mode an asynchronous ventricular pacing only takes place.

An MRI device uses a strong, constant magnet field having, for example, a nominal magnetic field strength of above 1T, for example, 1.5T, 3T or 7T. By superimposing the constant magnetic field with time-varying magnetic gradient fields a magnetic resonant effect is induced, which may be detected using RF detection coils for picking up signals within a patient's body to conduct an imaging of the patient. Herein, when a patient shall undergo an MRI examination, the patient typically is placed on a patient bed of the MRI device and, by moving the patient bed into a bore of the MRI device, is placed with a body part to be examined inside of the bore of the MRI device.

If a patient carrying an implantable medical device, such as a cardiac stimulation device, shall undergo an MRI examination, the implantable medical device shall be enabled to detect that the patient is approaching an MRI device such that operation of the implantable medical device may suitably be modified in order to reduce a risk of an impact of the MRI device, in particular the strong magnetic field of the MRI device, on the operation of the implantable medical device. The sensing device may, for example, be configured to measure a magnetic field strength at the location of the implantable medical device. In this case, for detecting whether a patient carrying an implantable medical device is in the vicinity of an MRI device, measurement values of the sensing device for detecting a magnetic field are examined. If it, for example, is found that a multiplicity of measurement values obtained from the sensing device of the implantable medical device indicate an increase of the strength of the magnetic field, it is assumed that a patient is placed on a patient bed of an MRI device and is moved, by moving the patient's bed with a substantially constant velocity, into the bore of the MRI device.

Alternatively or in addition, the sensing device may be configured to measure a gradient magnetic field sensor to enable the processing device to identify the presence of an MRI device.

Alternatively or in addition, the sensing device may be an RF field sensor for measuring an RF electromagnetic field of an MRI device to enable the processing device to identify the presence of an MRI device.

Alternatively or in addition, the sensing device may be a position sensor, a vibration sensor, or a sensor for detecting characteristic electrical signal patterns, as induced, for example, on the leads of the implantable medical device.

In another aspect, an external device operative in a medical system is configured to program at least one setting of an implantable medical device which has a switching function to switch from a normal operating mode to an MRI compatible operating mode in the presence of an MRI device. Herein, the external device is configured, based on a programming event relating to said at least one setting, to generate a notification prompting a user to confirm a continuing MRI compatibility of said MRI compatible operating mode after the programming event and/or to amend said at least one setting for achieving MRI compatibility.

In yet another aspect, a method for operating a medical system comprises: programming at least one setting of an implantable medical device using an external device, the implantable medical device having a switching function to switch from a normal operating mode to an MRI compatible operating mode in the presence of an MRI device; and generating, using the external device and based on a programming event relating to said at least one setting, a notification prompting a user to confirm a continuing MRI compatibility of said MRI compatible operating mode after the programming event and/or to amend said at least one setting for achieving MRI compatibility.

The advantages and advantageous embodiments of the system as described above equally apply also to the external device and to the method, such that it shall be referred to the above in this respect.

BRIEF DESCRIPTION OF THE DRAWINGS

Various features and advantages of the present invention may be more readily understood with reference to the following detailed description and the embodiments shown in the drawings. Herein.

DETAILED DESCRIPTION

Figure 1:
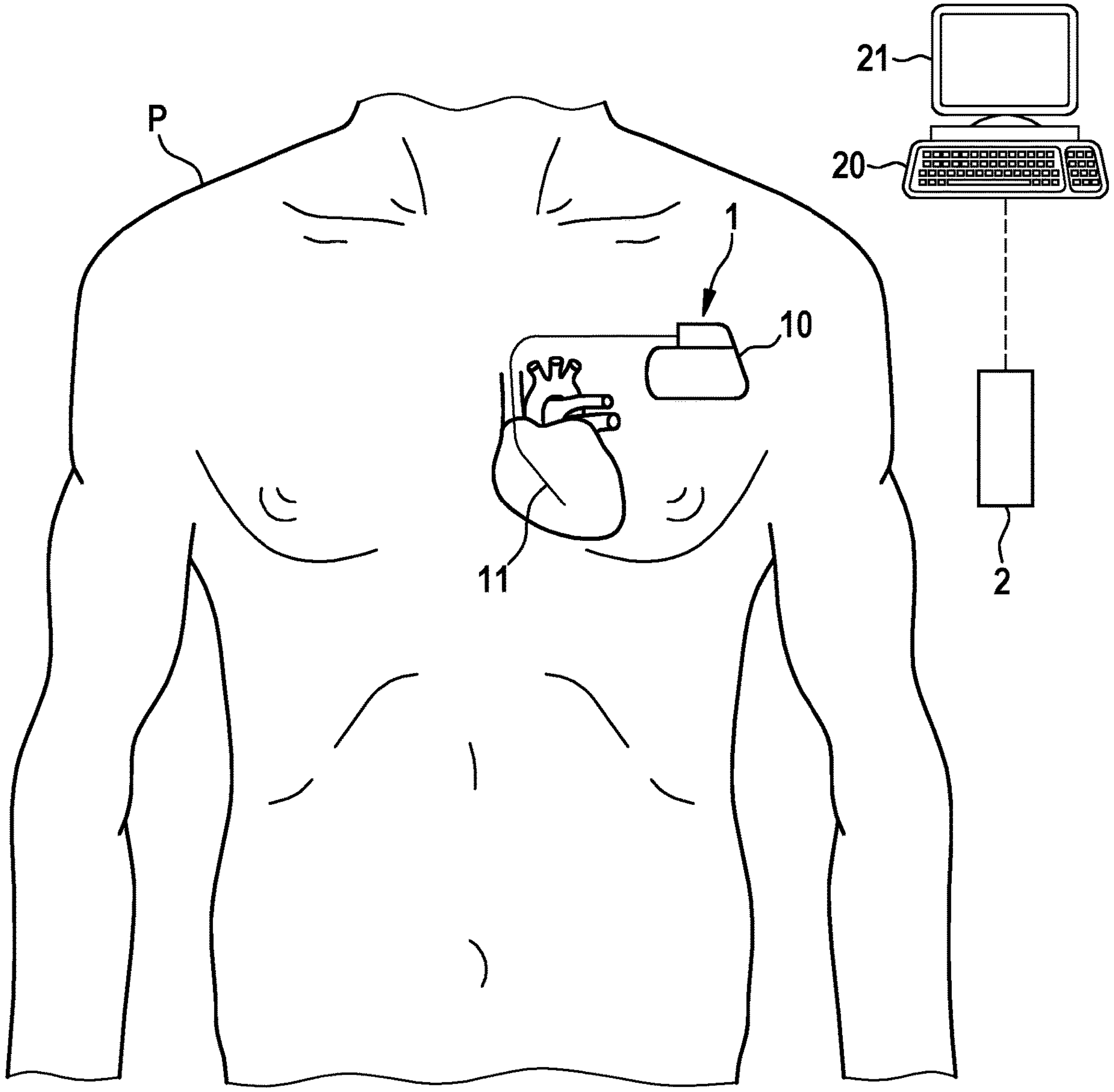
FIG. 1 shows a schematic illustration of an implantable medical device in a patient.

Subsequently, embodiments of the present invention shall be described in detail with reference to the drawings. In the drawings, like reference numerals shall designate functionally similar structural elements, if appropriate.

It is to be noted that the embodiments are not limiting for the present invention, but merely represent illustrative examples.

FIG. 1 shows a schematic illustration of an implantable medical device 1, for example, in the shape of a stimulation device, such as a pacing device or a defibrillation device. The implantable medical device 1 may, for example, comprise a generator 10 which, for example, as illustrated in FIG. 1, may be subcutaneously implanted into a patient, wherein an electrode 11 is connected to the generator 10 and extends from the generator 10 towards a region of interest, for example, the patient's heart, such that a therapy function may be provided at the region of interest, for example, in the patient's heart.

An implantable medical device 1 of this kind may, for example, be configured to provide a therapy function over a prolonged period of time, for example, a pacing function or a defibrillator function. The implantable medical device 1, for this, may be permanently implanted into a patient P and may function in a substantially autarkic manner, wherein a communication connection may be established with the implantable medical device 1 using an external device 2, for example, to program the implantable medical device 1 or to transfer, using, for example, telemetry, data from the implantable medical device 1 to the external device 2.

An external device 2 may communicate with the implantable medical device 1 using electromagnetic means, for example, by establishing an inductive coupling in between the implantable medical device 1 and the external device 2.

Figure 2:
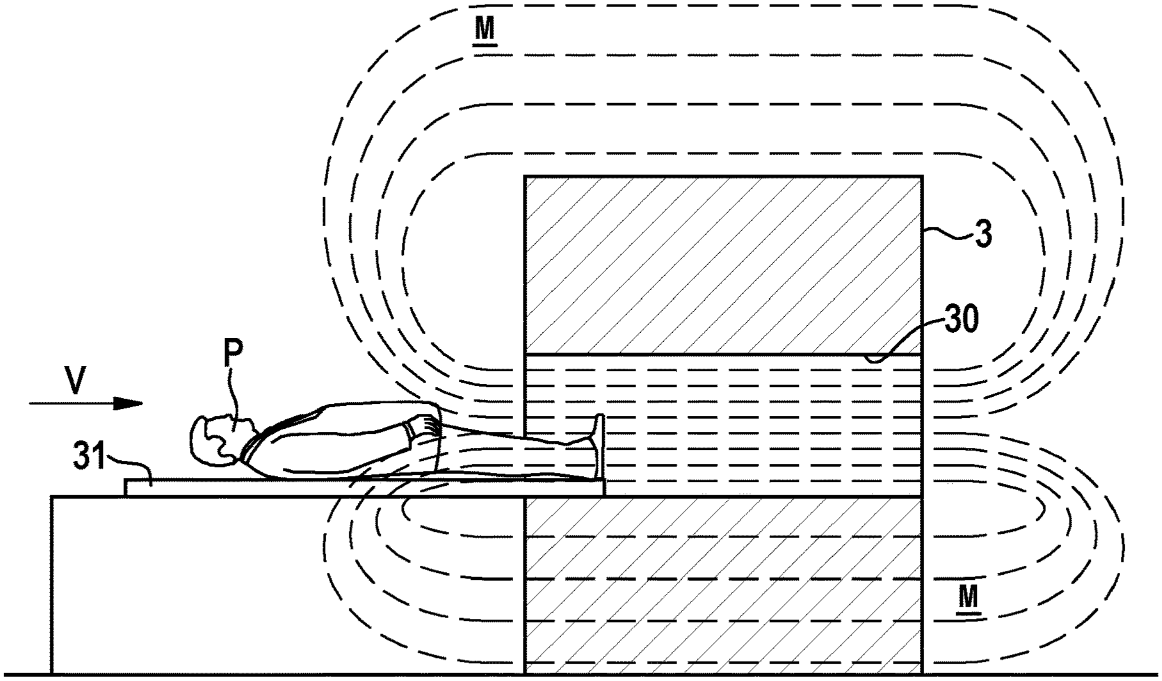
FIG. 2 shows a schematic drawing of an MRI device.

If, as schematically illustrated in FIG. 2, a patient P shall undergo an MRI examination using an MRI device 3, the patient P, carrying an implantable medical device 1, is introduced into a bore 30 of the MRI device 3 by placing the patient P on a patient bed 31 and by continuously moving, using an electro-motoric drive of the patient bed 31, the patient P into the bore 30 in a movement direction V. When moving the patient P into the bore 30 of the MRI device 3, the patient P herein is brought into the range of a constant magnetic field M of the MRI device 3, the magnetic field M generally having a maximum magnetic field strength (corresponding to the magnetic flux density B and indicated usually in Tesla [T]) within the bore 30. Hence, when the patient P is moved into the bore 30 of the MRI device 3, the magnetic field strength of the magnetic field M at the location of the implantable medical device 1 will steadily increase.

Caused by a magnetic field M of an MRI device 3 electrical signals may be induced within an implantable medical device 1. Hence, it shall be detected if an implantable medical device 1 comes into the range of an MRI device 3, such that operation of the implantable medical device 1 can suitably be modified in order to avoid a disturbance of operation by the MRI device 3.

Figure 3:
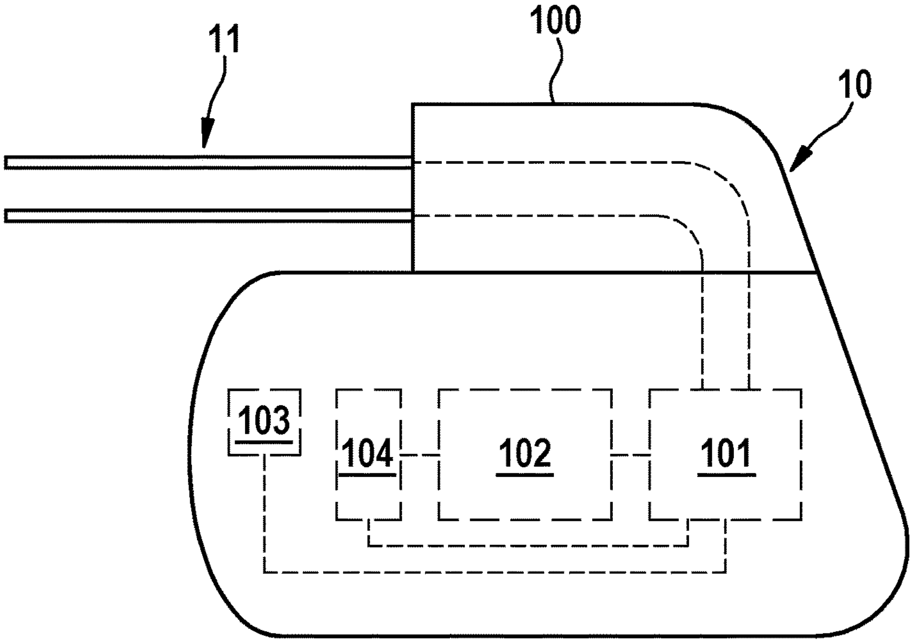
FIG. 3 shows a schematic drawing of an implantable medical device.

FIG. 3 illustrates an embodiment of a generator 10 of an implantable medical device 1, for example, in the shape of a stimulation device such as a pacemaker device or a defibrillator device. Included in a housing of the generator device 10 is a processing device 101, implemented, e.g., by electronic circuitry on a circuit board, which serves to control operation of the generator 10 for transmission of electrical stimulation energy via the electrodes 11 connected to a connector block 100 of the generator 10, and for analyzing sense signals received, e.g., via the electrodes 11 to provide for a therapy aligned to an activity of, for example, the patient's heart.

The generator 10 further comprises an energy storage 102 in the shape of a battery, a sensing device 103, for example, in the shape of a GMR sensor for sensing magnetic fields, and a communication device 104 for establishing a communication connection, for example, to an external device 2, as illustrated in FIG. 1.

The sensing device 103 is connected to the processing device 101 and is configured to conduct measurements yielding measurement values indicative of a magnetic field strength at the location of the sensing device 103. The sensing device 103 may, for example, be configured to conduct measurements at a specified sampling rate, for example, at a rate in between 1 Hz and 50 Hz, for example, 4 Hz. The sensing device 103 provides (discrete) measurement values to the processing device 101, which are analyzed by the processing device 101 and are used to identify the presence of an MRI device 3.

Figure 4:
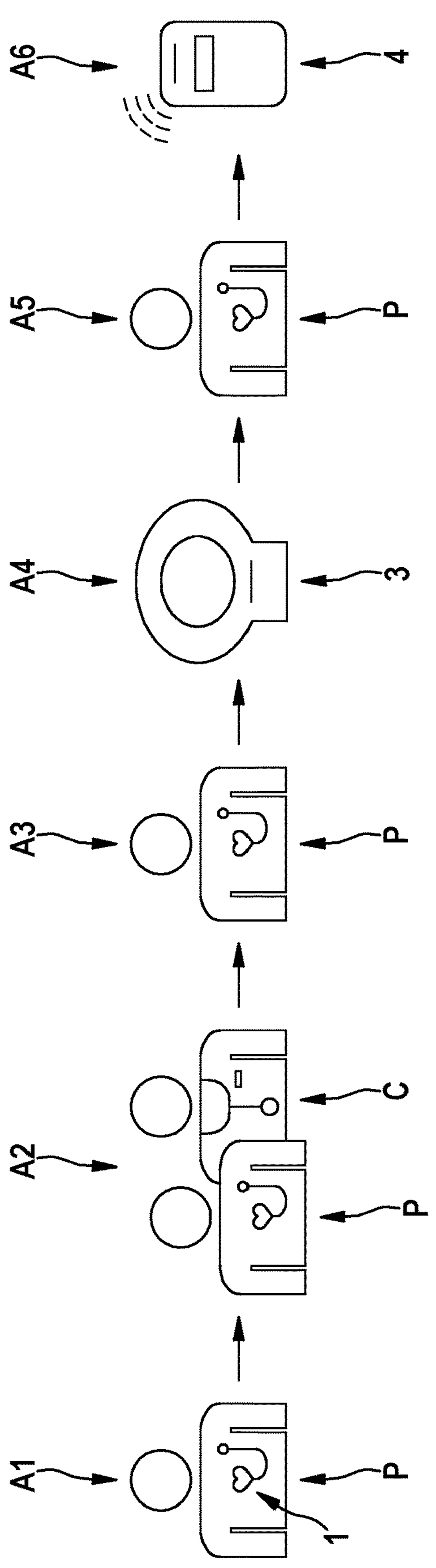
FIG. 4 shows a schematic drawing of preparatory steps for conducting an MRI examination on a patient carrying an implantable medical device such as a pacemaker device.

Referring now to FIG. 4, if a patient P carrying an implantable medical device 1 (for example, in the shape of a pacemaker device, such as a CRT device) has to undergo an MRI examination, the patient P typically has to visit a physician C such that the physician C may adapt operation of the implantable medical device 1 in order to avoid a malfunction of the implantable medical device 1 during MRI examination (steps A1, A2 in FIG. 4). In the course of adaption, for example, an MRI compatible operating mode is enabled in which a stimulation function of the implantable medical device 1 is switched off, or in which the stimulation function is adapted such that the implantable medical device 1 may safely operate in the presence of electromagnetic fields as caused by an MRI device 3.

Such adaption of the configuration of the implantable medical device 1 should take place within a rather short time range prior to the MRI examination, for example, within 14 days prior to the MRI examination. The patient P may then undergo the MRI examination (steps A3, A4), wherein the MRI compatible operating mode is activated once the presence of the MRI device 3 is detected by the implantable medical device such that during the MRI examination the implantable medical device operates according to its modified, MRI compatible operating mode. Subsequent to the MRI examination data may be reported to a home monitoring system 4 (steps A5, A6), and the implantable medical device 1 may switch back to resume normal operation.

In a conventional scenario, a patient P hence must visit a physician C prior to an MRI examination, which must suitably configure the implantable medical device 1 in order to enable an operation which is adapted to a potential interaction with electromagnetic fields of an MRI device 3.

Figure 5:
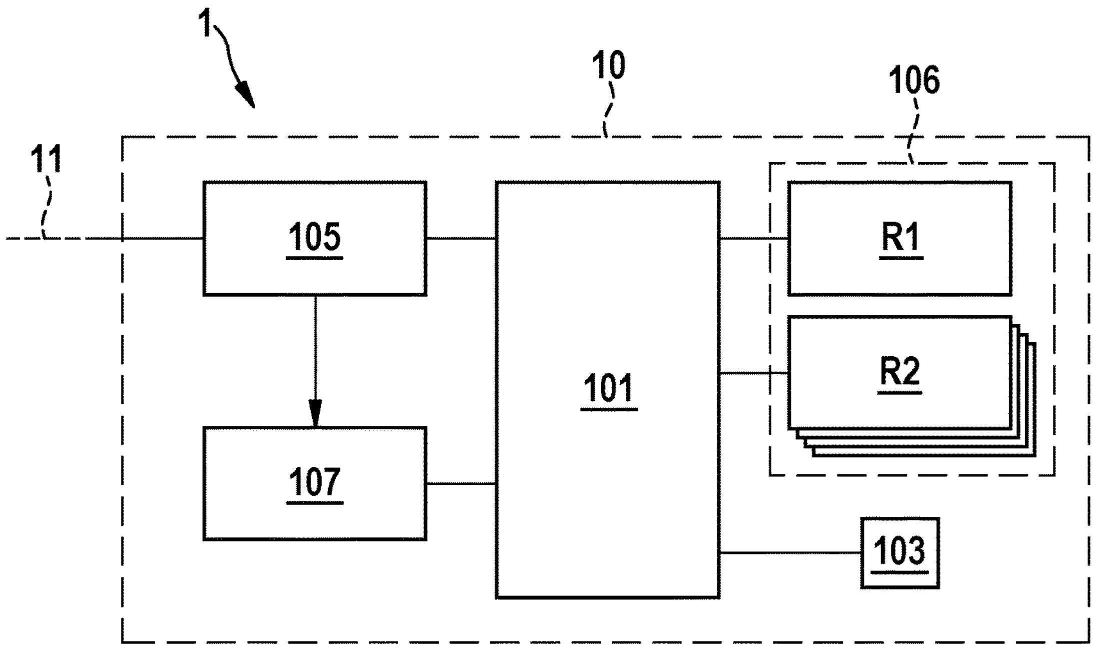
FIG. 5 shows a schematic drawing of an implantable medical device being configured for adapting operation in case of a presence of an MRI device.

Referring now to FIG. 5, an implantable medical device 1 may be adapted for an automatic selection of configuration if a presence of an MRI device 3 is detected based on measurement data obtained from a sensing device 103.

The implantable medical device 1, as shown in FIG. 5, comprises a processing device 101 which controls operation of the implantable medical device 1, in particular to control a stimulation module 105 configured to transmit stimulation energy towards electrodes 11 attached to a generator portion 10 of the implantable medical device 1 and to receive sensing data from the electrodes 11. For example, in one embodiment the implantable medical device 1 may be configured to provide for an anti-bradycardia stimulation, for which a therapeutic function is triggered once a bradycardia is detected in order to provide for a pacing counteracting the bradycardia.

Generally, in a default, normal operating mode the processing device 101 may, for example, provide for a stimulation based on sensed measurement data, in order to, for example, provide a stimulation in a synchronous fashion in synchronicity and triggered by sensed activity. For example, in a normal operating mode the processing device may be configured to operate in a so-called VVI mode, relating, for example, to a ventricular anti-bradycardia pacing, or a DDD mode, relating, for example, to a dual-chamber anti-bradycardia pacing.

In case the processing device 101 identifies, based on measurement data obtained from a sensing device 103 (such as a GMR sensor for measuring a magnetic field strength at the location of the implantable medical device 1) the presence of an MRI device 3, the processing device 101 is configured to automatically adapt operation of the implantable medical device 1 in that the processing device 101 switches to an MRI compatible operating mode. For this, the processing device 101 switches to a program routine R1, R2, which is stored in a program memory 106 and implements an MRI compatible operating mode in that it provides for a suitable operation of the implantable medical device 1 in the presence of electromagnetic fields of an MRI device 3. In particular, by means of the program routine R1, R2 it is made sure that malfunctions due to interaction with electromagnetic fields of the MRI device 3 are avoided.

In the program memory 106, different program routines R1, R2 may be stored, which provide for different MR compatible operating modes. Herein, the processing device 101 may be configured to select one of the program routines R1, R2 based on an analysis of information, e.g., of a patient's condition, e.g., a history of heart rate information, as stored in a memory 107.

A program routine R1, R2 may, for example, represent an OFF mode in which a stimulation function is switched off, such that, if the implantable medical device 1 is operated according to the particular program routines R1, R2, no stimulation takes place once the patient P is in the vicinity of an MRI device 3.

Another program routine R1, R2 may represent an asynchronous mode in which a stimulation takes place, but in an asynchronous fashion, i.e., without sensing data and without basing a stimulation, such as a pacing action, on sensed data. The asynchronous mode may, for example, be a VOO or a DOO mode.

The switching to a program routine R1, R2 takes place once the processing device 101, based on readings of the sensing device 103, identifies the presence of an MRI device 3. The sensing device 103 herein may, for example, be configured to measure a magnetic field strength for identifying, for example, a rise of the magnetic field strength. Alternatively, the sensing device 103 may be adapted to measure a gradient field vector, an RF field, a position, a vibration, or a characteristic electrical signal pattern as, for example, induced on the electrodes 11. Multiple sensors measuring different measurement quantities may be used in combination.

Once the processing device 101 identifies that the patient P no longer is in the presence of an MRI device 3, the processing device 101 switches back to the normal operating mode, by, for example, switching on a stimulation function or switching to a synchronous mode.

By means of the processing device 101, hence, an automatic switching of operation to a program routine R1, R2 which is suitable for use during an MRI examination is provided. This makes it possible for a patient P to undergo an MRI examination without specific preparation, in particular without having to visit a physician C (as shown in FIG. 4) for the purpose of configuring the implantable medical device 1 prior to undergoing the MRI examination. The burden for the patient P hence is reduced, while at the same time saving time and costs.

Referring now again to FIG. 1, the external device 2 may be used to change settings of the implantable medical device 1, such that operation of the implantable medical device 1 may be modified according to a programming of settings using the external device 2. A change of settings herein may take place in order to adapt a certain function of the implantable medical device 1, for example, to switch on or off a defibrillation function or an ATP function, or to switch from a synchronous stimulation mode to an asynchronous stimulation mode or vice versa.

In addition, a change of settings may take place if a hardware configuration of the implantable medical device 1 changes, for example, if an electrode 11 is invasively added to or removed from the implantable medical device 1, making it necessary to adapt the operation of the implantable medical device 1 to ensure a proper operation according to the modified hardware configuration of the implantable medical device 1.

Figure 6:
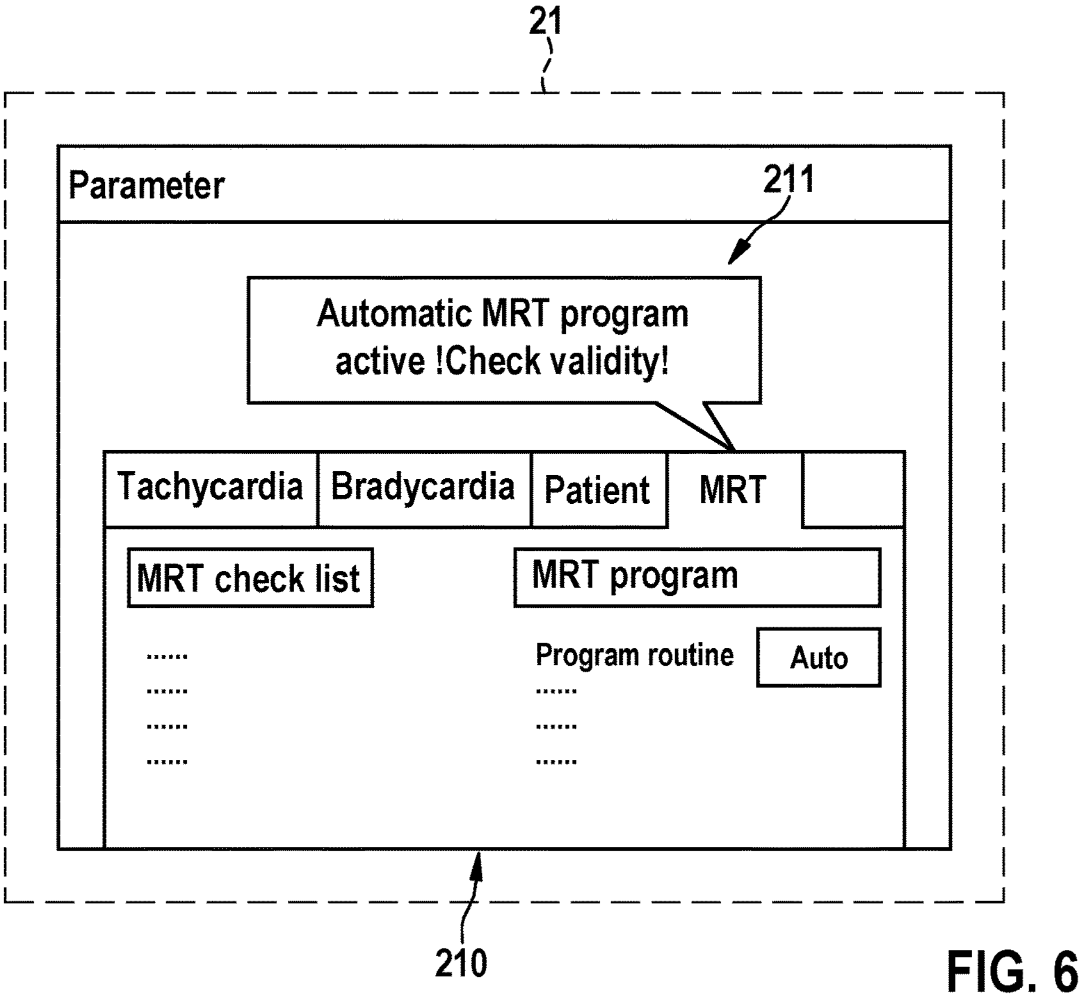
FIG. 6 a schematic view of a menu as displayed on a display device.

A change in settings using the external device 2 may, for example, take place using an input device 20, for example, in the shape of a keyboard, and a display device 21, which may be connected to the external device 2 or may be an integral part of the external device 2. Via the input device 20 and the display device 21, for example, a menu 210 as shown in FIG. 6 may be accessed, wherein via the menu 210 different settings relating to different categories, in particular relating to a hardware configuration and a software configuration, may be accessed and modified, wherein a change in settings on the user interface of the external device 2 shall cause a corresponding change in settings in the implantable medical device 1.

If one or multiple settings are changed in a programming event on the external device 2, this may also affect the MRI compatibility of the MRI compatible operating mode. Hence, in case of a programming event in which one or multiple settings are changed on the external device 2, a notification 211, for example, in the shape of an output message is displayed on the display device 21, the notification 211 prompting the user to confirm a continuing MRI compatibility of the MRI compatible operating mode even with the new settings.

Hence, the user is required to enter a confirmation by which it is confirmed that even after the programming event and the corresponding change in settings the MRI compatible operating mode remains MRI compatible. The external device 2 herein may be configured such that the change in settings is transferred to and activated on the implantable medical device 1 if and only if the user enters the confirmation.

By means of the notification 211 the user may be asked to input a confirmation confirming the continuing MRI compatibility of the MRI compatible operating mode, or otherwise to again change the settings and then confirm MRI compatibility, or to revert to the old settings. The notification 211 herein may be displayed until a confirmation is entered, such that the user is forced to react to the notification 211 in order to activate a change in settings on the implantable medical device 1.

A notification 211 may be displayed visually on the display device 21, or acoustically as an acoustic message. In addition or alternatively, a message may be communicated to another (remote) system, or may be printed out together with a data report or the like.

By generating and displaying the notification 211 in the event of programming settings using the external device 2, it is made sure that MRI compatibility of the implantable medical device 1 is checked and ensured, hence improving reliability of operation and easing due care during a programming of settings of an implantable medical device 1.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

LIST OF REFERENCE NUMERALS

1 Implantable medical device (pacemaker device)
10 Generator
100 Connector block
101 Processing device
102 Energy storage
103 Sensing device
104 Communication module
105 Stimulation module
106 Program memory
107 Memory
11 Electrode
2 External device
20 Input device
21 Display device
210 Menu
211 Notification (prompt message)
3 MRI device
30 Bore
31 Patient bed
4 Home monitoring system
A1-A6 Steps
C Clinician
M Magnetic field (magnetic flux density)
P Patient
R1, R2 Program routine
V Moving direction

The invention claimed is:

1. A medical system, the system comprising: an implantable medical device having a switching function to switch from a normal operating mode to an MRI compatible operating mode in the presence of an MRI device; and an external device for programming at least one setting of the implantable medical device; wherein the external device is configured, based on a programming event relating to said at least one setting, to generate a notification prompting a user to confirm a continuing MRI compatibility of said MRI compatible operating mode after the programming event and/or to amend said at least one setting for achieving MRI compatibility.

2. The medical system of claim 1, wherein the external device comprises a display device for visually outputting said notification.

3. The medical system of claim 1, wherein the programming event relates to a change in a hardware configuration of the implantable medical device.

4. The medical system of claim 1, wherein the programming event relates to a change in a software configuration of the implantable medical device.

5. The medical system of claim 1, wherein the programming event relates to a change in a setting of a therapeutic function or a diagnostic function of the implantable medical device.

6. The medical system of claim 1, wherein the external device is configured to effect said at least one setting of the implantable medical device only if said continuing MRI compatibility of said MRI compatible operating mode is confirmed by a user in reaction to said notification.

7. The medical system of claim 1, wherein the external device is configured to generate said notification only if said switching function is enabled for switching from said normal operating mode to said MRI compatible operating mode in the presence of an MRI device.

8. The medical system of claim 1, wherein the implantable medical device comprises a sensing device for sensing a measurement quantity indicative of a presence of an MRI device, and a processing device for controlling operation of the implantable medical device and for identifying a presence of an MRI device based on measurement values obtained from the sensing device.

9. The medical system of claim 8, wherein the implantable medical device comprises a program memory configured to store at least one program routine for operating the implantable medical device in said MRI compatible operating mode, wherein the processing device is configured to switch to said at least one program routine for controlling operation of the implantable medical device in the presence of an MRI device.

10. The medical system of claim 9, wherein said at least one program routine represents an OFF mode in which a stimulation function is switched off.

11. The medical system of claim 9, wherein said at least one program routine represents an asynchronous mode employing an asynchronous stimulation.

12. An external device-operative in a medical system, the external device being configured to program at least one setting of an implantable medical device which has a switching function to switch from a normal operating mode to an MRI compatible operating mode in the presence of an MRI device; wherein the external device is configured, based on a programming event relating to said at least one setting, to generate a notification prompting a user to confirm a continuing MRI compatibility of said MRI compatible operating mode after the programming event and/or to amend said at least one setting for achieving MRI compatibility.

13. A method for operating a medical system, comprising: programming at least one setting of an implantable medical device using an external device, the implantable medical device having a switching function to switch from a normal operating mode to an MRI compatible operating mode in the presence of an MRI device; wherein generating, using the external device and based on a programming event relating to said at least one setting, a notification prompting a user to confirm a continuing MRI compatibility of said MRI compatible operating mode after the programming event and/or to amend said at least one setting for achieving MRI compatibility.

* * * * *